United States Patent [19]

Runyon et al.

[11] Patent Number: 4,550,728

[45] Date of Patent: Nov. 5, 1985

[54] EPILATOR

[75] Inventors: Wayne Runyon, Ridgewood; Larry Hower, New York, both of N.Y.

[73] Assignee: L. P. Systems Corporation, New York, N.Y.

[21] Appl. No.: 410,456

[22] Filed: Aug. 23, 1982

[51] Int. Cl.⁴ .............................................. A61B 17/41
[52] U.S. Cl. ................................. 128/303.18; 128/908
[58] Field of Search ...................... 128/303.13, 303.14, 128/303.17, 303.18, 908

[56] References Cited

U.S. PATENT DOCUMENTS

| | | | |
|---|---|---|---|
| 2,238,344 | 4/1941 | Schuler et al. | 128/303.18 |
| 4,167,187 | 9/1979 | Biagi | 128/303.18 |
| 4,224,944 | 9/1980 | Roberts | 128/303.18 |
| 4,301,801 | 11/1981 | Schneiderman | 128/303.14 |
| 4,321,926 | 3/1982 | Roge | 128/303.18 |
| 4,352,357 | 10/1982 | Capuno | 128/303.13 |
| 4,372,315 | 2/1983 | Shapiro et al. | 128/303.18 |

Primary Examiner—Lee S. Cohen
Attorney, Agent, or Firm—McAulay, Fields, Fisher, Goldstein & Nissen

[57] ABSTRACT

Epilator apparatus for outputting epilator pulses comprising a radio frequency generator for generating RF energy. A maximum intensity monitor circuit is coupled to the RF generator and a maximum timing monitor circuit is coupled to the RF generator to predetermine the maximum duration of RF energy output. A power supply including an overvoltage control responsive to the maximum timing monitor circuit and responsive to the maximum intensity monitor circuit for cutting off power including the RF energy when a voltage is reached in excess of a pre-set value.

20 Claims, 5 Drawing Figures

EPILATOR

BACKGROUND OF THE INVENTION

1. Field of the Invention

This invention relates to a high frequency needle-type epilator.

More particularly, the invention is concerned with safety features which are incorporated into our improved epilator.

2. Description of the Prior Art

Needle-type high frequency epilators are known. Some of these are generally referred to as Kree brand model 1001; 2000, and 700; also known are the Instantrons brand Model SS-69 and Proteus brand Model EP 2000.

The prior art uses low accuracy components and RC type timing circuits which are not exactly repeatable, they cannot be set with a high degree of accuracy.

Uncontrolled high level RF output due to self-oscillation is elminated which was potentially dangerous.

SUMMARY OF THE INVENTION

The epilator of the present invention is primarily concerned with safety factors.

The design of the novel epilator incorporates a number of safety circuits and features which have been referred to in other sections of this description. This section will summarize and detail the safety considerations.

The safety circuits act to prevent undesired and possibly harmful operation of the epilator. Since an electronic device needs electrical power to operate, many of the safety features act in such a way as to stop the flow of electric current from the power supply.

The final section of the power supply is the overvoltage monitor section. This is a voltage-sensitive switch which grounds (crowbars) the output of the power supply in the event the power supply should have a regulator failure and put out voltage in excess of the desired value. We have utilized the overvoltage monitor for additional safety functions as follows.

The novel epilator has a maximum timing monitor circuit, the function of which is to prevent the epilator from out-putting for more than the maximum preset time.

The maximum length of RF pulse time normally available from the epilator is 0.0999 second (999/10,000 of a second). The maximum timing monitor is set to activate should the epilator put out a pulse longer than 0.140 second. If an excessively long pulse is sensed, the maximum timing monitor circuit activates the overvoltage protection circuit and the overvoltage protection circuit grounds (crowbars) the output of the power supply. With a grounded/shorted power supply, there can be no RF output. This is also internally controlled and subject to operator control.

The same type of operation is affected by the maximum intensity monitor. Should a voltage in excess of a factory preset value be sensed by the maximum intensity monitor circuit, the overvoltage circuit is activated and the power supply output is grounded.

Should a component failure occur that will not result in excessive timing or intensity, but will result in excessive current being drawn from the power supply, the current limiting circuit is activated and the supply goes into a low output self-protect mode.

The footswitch circuits are designed to ignore operator variations and give repeatable, reliable performance.

The operator indicators, light and tone, are driven by a circuit that senses actual output; no output-no indication. This prevents operators from going through the motions of epilation with an inoperable machine, thereby only tweezing the hair.

The RF producing section is completely shielded by a metal enclosure. All leads from the RF section are bypassed or shielded to prevent undesired RF radiation.

In some epilator designs DC current is applied to the power amplifier continuously. If some instability, from overheating for example, should arise the power amplifier could start to self oscillate. This is extremely dangerous because the power output would be very high and continuous, and not under the control of the operator. Often it does occur without the knowledge of the operator, only to be discovered as the needle is being inserted or withdrawn from the follicle. Permanent tissue damage would be the result.

The novel epilator is designed so that DC current is applied to the power amplifier only during the epilation pulse. The previously cited self oscillation cannot occur in the novel epilator. See Discussion of FIG. 4 for further explanation.

The epilator according to the invention differs from heretofore known epilators by virtue of the following features:

a. the use of an epilation pulse of higher peak power and shorter pulse length than currently marketed designs. This results in less tissue damage and greater comfort.

b. Precise state of the art circuit design which ensures exact repeatable performance. Also, one machine may be substituted for another and provide the same performance.

c. fail safe features that are completely absent from all other epilators presently marketed. These features are discussed and explained hereinafter.

The major operational difference is the use of a pulse of higher peak power and shorter pulse duration than many other epilators. This design has the capability to put out a pulse of RF energy of 20 Watts for the duration of the timing cycle. The 20 Watt value is 3 dB., greater (about twice) than some other epilators.

The higher power level was designed into the unit as a result of observing the operation of lower power epilators in removing hair.

The maximum timing available in this design is limited to 0.0999 second whereas most epilators provide up to 1.0 second of pulse length.

Some background information is necessary in order to understand the basis of the design.

Presently, all operators have the option of working with two types of electrodes:

1. Standard bare wire needles (old fashioned)

OR

2. Insulated bulbous probes

Standard bare wire needles dissipate current along their entire shaft with an ultimately weakened current reaching the area that is to be destroyed making for inefficient treatment and necessitating repeat removals of the same hair. If the machines are set at extremely high levels with long impulses to compensate for this bleed out of current, intolerable pain and scarring will ensue.

Standard bare wire needles have sharp cutting edges that can pierce follicle walls or slip through beyond the desired depth resulting in current being applied directly into the skin, again resulting in excessive pain and destruction of live tissue unrelated to hair. Further, when the operator attempts to lift the hair out of the skin, it behaves as though not treated at all and is totally resistant, necessitating further insertions and the application of more current that further compounds the initial damage, or the hair is simply tweezed out and will regrow or ingrow if the hair was severed during the insertion.

Standard bare wire needles are of rigid construction and cannot accommodate distorted follicles at all. Shallow insertions are made, current is indiscriminately applied and the hair is manually tweezed in the line of direction in which it grows. This is repeated several times in an attempt to straighten the follicle it is a very questionable practice.

The combination of standard epilators and standard bare wire needles, at best, produce a degree of heat sufficient to electro coagulate a given area. Electro coagulation is insufficient to immediately and permanently remove hair. On the other hand, insulated bulbous tip probes combined with the novel epilator produce the degree of heat sufficient to dessicate the germinative area of the hair safely and immediately. The dessication is done by the nearly instantaneous heating action of the RF energy. The short pulse high peak power design of the inventive epilator complements the probe perfectly and safely, in view of the probe's unique characteristics described below.

Insulated Bulbous tip probes are insulated completely along their shafts to prevent current bleedouts. This insures that whatever current and timing loads are set up are delivered. Current is concentrated at, and dispersed through the uninsulated tip only.

When the probe is properly inserted and in place, the footswitch is depressed and a pulse of RF energy dessicates the dermal papilla of the hair. Dessication is accomplished by heating. The RF pulse is usually short: 0.040 sec to 0.200 sec., depending on the hair. The probe is withdrawn and the hair is lifted out of the follicle with forceps.

Insulated Bulbous tip probes have precision shaped tips that can enter only a natural opening, assuring the accuracy of every insertion. If an attempt is made to penetrate the skin; the probe will literally "bounce off" the skin or crumple under pressure.

The bulbous tip enables the operator to gently straighten distorted follicles without piercing or severing the follicle walls. A contributory factor that we should mention here is that the blade of the probe (the area immediately behind the tip) is totally flexible, so that in fact the operator is simultaneously able to bend the probe to accommodate the distortion and the bulbous tip prevents any severing action.

The bulbous tip further enables the operator to "feel" the natural stop or barrier presented by the "bulb" of the hair further ensuring "on target delivery of current".

Presently, no machines on the market operate at precise levels continuously and it is for this reason that the novel epilator was designed in coordination with insulated bulbous probes in order to achieve peak efficiency, with safety. The end result is immediate permanent hair removal without tissue damage.

We have observed a number of currently marketed standard epilators in operation and, when working properly, many will electro coagulate small and medium hairs adequately. However, for thick, heavy hairs, such as a man's beard, more material must be heated to achieve removal of the hair. If the epilator lacks adequate RF power to do this with a short pulse, the operator usually adjusts the epilator for a long pulse duration. In many instances the operator will use two or more pulses for the same hair. With a low power (7–10 Watts) epilator, the heating of the skin must be more extensive in area in order to reach the temperature needed at the base of the hair. The reason for this is that the skin conducts the heat away from the base of the hair and in order to bring up the temperature to the required level, the pulse must be much longer. This more extensive heating causes more swelling and painful discomfort to the subject. Most of these standard epilators have a timing section which will allow up to a 1.0 second of RF pulse duration. PLEASE NOTE the maximum pulse length available on our epilator is 0.0999 second.

RF power output of these standard epilators is not easy to measure accurately but our study indicates some are capable of 10 Watts power output.

Measurements of pulse duration indicate large variation from machine to machine of even the same model. One unit had 0.040 second pulse at the "0" timing setting while another had a 0.080 second pulse at "0".

By observation and extrapolation of RF/Timing values, it is strongly indicated that a somewhat higher power epilator using a short pulse duration can do a superior job of epilation with a minimum of discomfort and irritation to the subject.

It is our understanding that the impedance of human skin is approximately 800 to 900 ohms. This impedance is used so that the output impedance of the transmitter is matched with the human impedance of 800 to 900 ohms. The output network impedance is preferably targeted at 850 ohms and is tuned to this type of load. Others believe that the impedance is 1500 ohms even though we have found that skin impedance is 850 ohms at 27.120 MHz RF energy. For this purpose, the prior art places a 50 ohm impedance in parallel with the human body impedance. It is understood that Kree did try impedance matching, but at 1500 ohms.

The novel epilator incorporates a maximum timing monitor which is made up of an RC network which is coupled to the output of the RF detect circuit. Should the RF output cycle continue for more than 0.14 seconds, the RC network would activate a Schmitt-trigger which would in turn activate the over-voltage protection circuit. If the RF circuit is active for more than 0.14 seconds, the power supply is completely cut-off. The machine according to the invention is shut down in a time period which is less than the time period other machines would continue to malfunction and the operator became aware that the tissue of a person or subject was being burned.

A maximum intensity monitor is provided which is coupled to the output of the intensity control circuit by means of a voltage divider. The voltage divider is designed to keep a Schmitt-trigger below its switching point; this is approximately 50% of the supply voltage during normal operation.

If the intensity control voltage exceeds the maximum pre-set value, the Schmitt-trigger switches, thus activating the over-voltage protection circuit (see 25, FIG. 2).

If the machines self-oscillate burning of the skin occurs. With this invention, self-oscillation is prevented by three means: (1) a degenerative feedback circuit in the power amplifier; (2) applying d.c. to the amplifier stages only during the epilator pulse time; and (3) maximum time monitor.

It is an object of the invention to provide timer circuits with built-in protection to prevent the circuits from being retriggered during an occurring epilator cycle, thus extending the epilation period for longer than the prescribed length.

Other features of the invention are the timing, intensity and footswitch controls.

Specifically, the timing is controlled by a high accuracy Quartz clock. 1000 increments of repeatable timing selected by easy to set rocker switches. The intensity is controlled by integrated circuits. 1000 increments of repeatable output intensity selected by easy to set rocker switches. The footswitch includes circuits which provide repeatable timing and ignore variations in operator's use of footswitch. Additionally, the power supply includes integrated circuit regulators which provide extremely stable voltage for machine operation. Overvoltage and overcurrent protection is built in. Solid state circuitry is included for maximum reliability.

A further object is the provision of a timing circuit which has small increments to provide for predetermined and exact levels of treatment for the individual so that it is repeatable for the same time period for different treatments. This permits the use of different machines and different operators, with the characteristic of the individual determining the time setting.

The intensity control also operates in a similar manner so that it can be repeatably set for the individuals needs.

Other objects, advantages and the nature of the invention will become readily apparent from the detailed description of the invention described in connection with the accompanying drawings.

DESCRIPTION OF THE PREFERRED EMBODIMENTS

Figure 1:
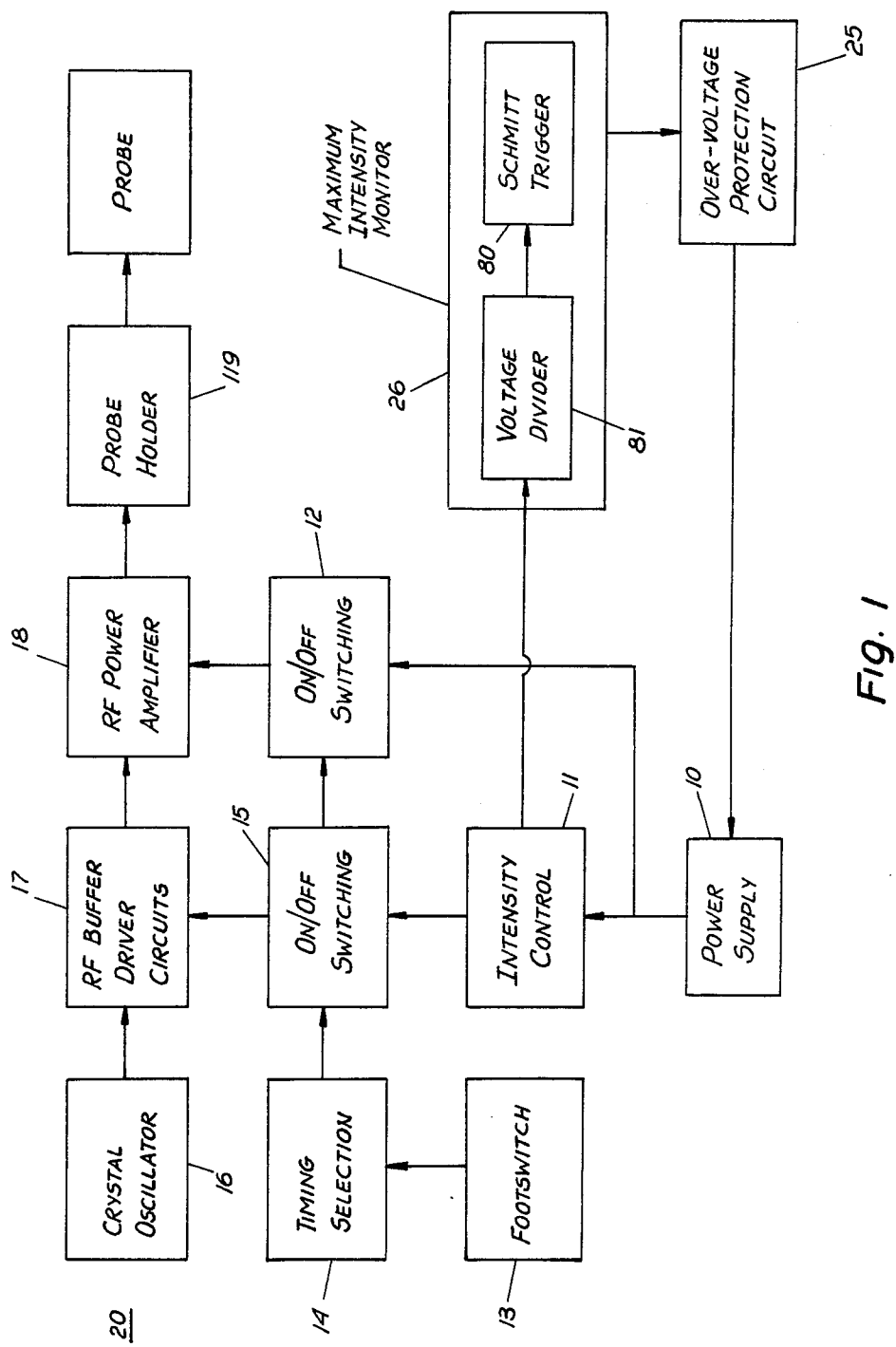
FIG. 1 is a block diagram of the major components of the invention for carrying out the major functions of the invention.

Referring now more particularly to the drawings which illustrate the best mode presently contemplated for carrying out the inventions, the epilator system according to the present invention includes OEM open frame AC rectified regulated power supply 10 having its output coupled to an intensity control circuit 11 and an on/off switching control 12. Footswitch 13 which is operator controlled is connected with a timing selection circuit 14 whose output is connected with a second on/off switching 15. Output of the intensity control 11 is coupled with the input to second on/off switching 15; the outputs of both on/off switching 12, 15 are coupled with a RF-radio frequency section 20. RF section 20 includes crystal occillator 16, RF buffer driven circuits 17 and RF power amplifier 18 to provide a 27.120 MHz output to a probe hold 119 and 19 which are schematically shown.

The crystal oscillator 16 provides the RF section with the frequency at which it operates and controls RF buffer driving circuits 17 which is only rendered operative when on/off switching 15 is on. The output of circuits 17 is coupled to radio frequency power amplifier 18 which is only rendered operative in response to on/off switching 12 being on and circuits 17 being operative to transmit a radio frequency to amplifier 18, and the output of 18 is fed through probe holder 119 to probe 19.

The power supply voltage is adjusted for a particular voltage, the supply will deliver the set voltage with very little variation (±0.10%). The current can be limited to a preset value also. Finally, the supply 10 is coupled to an overvoltage protection circuit 25 to shut down the supply in the event a component failure in the power supply regulator circuit should make the supply put out more than the desired voltage.

Maximum intensity monitor circuit 26 includes a Schmitt-trigger 80 having an input and one output. The input is coupled to voltage divider 81 which is connected with the output of intensity control 11. The output of the Schmitt-trigger is coupled to over-voltage protection circuit 25.

We utilize the circuit features of the power supply to advantage in the overall design of the epilator.

1. The current limiting feature is factory preset to limit the total amount of DC power to a safe value. Should a component or operational failure occur, causing the potential for current in excess of the desired value to be drawn, the current limiting circuit is activated and the power supply output is reduced to a very low value.
2. The overvoltage monitor/protection circuit (crowbar) is connected to other safety circuits in order to shut down the DC power supply in the event of excessively high RF output or an excessively long timing pulse. See further details on this aspect in the Safety Consideration section.

POWER SUPPLY SPECIFICATIONS

Figure 2:
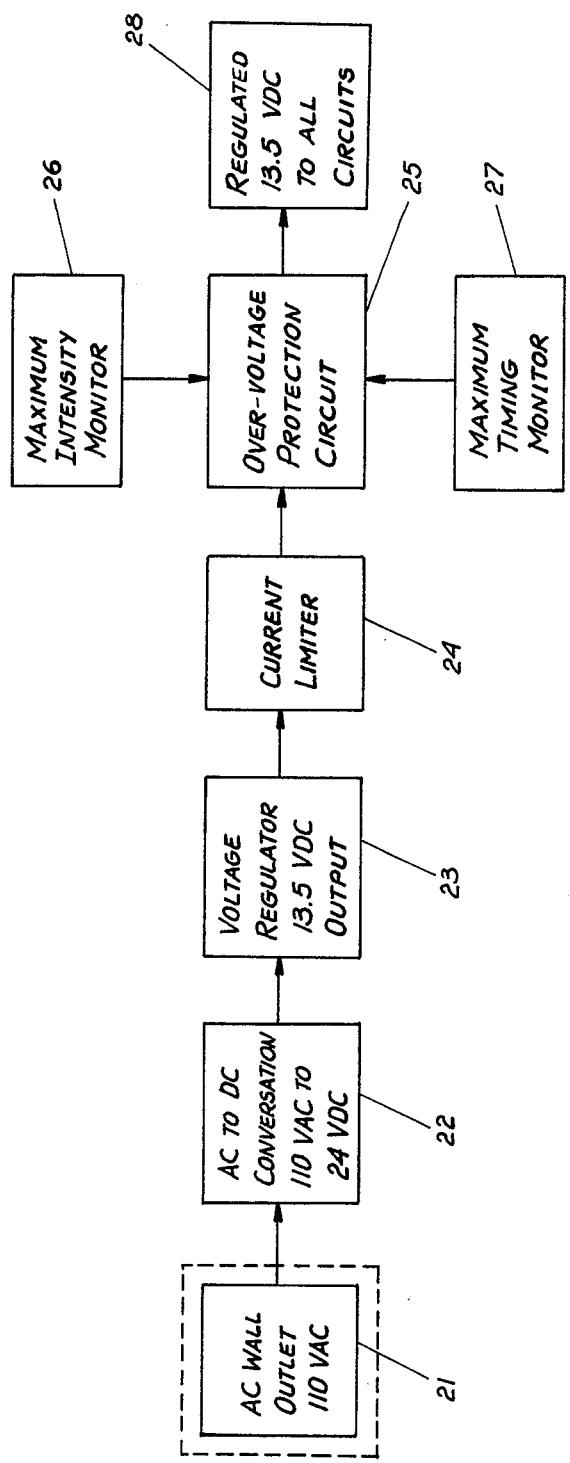
FIG. 2 is a block diagram of the power supply.

Input: 110 VAC; 60 HZ; 0.9 AMPS
Output:
  13.5 VDC
  Maximum 3.4 AMPS
Line and Loan Regulation: 0.10%
Ripple and Noise: 1.mV RMS, 5 mv P-P
Overvoltage Protection:
  Type-Crowbar
  Response time-10 microseconds
Current Limited Referring now more particularly to FIG. 2 which illustrates one preferred embodiment to provide for the foregoing features and a 13.5 VDC regulated voltage to all circuits. Wall outlet or plug 21 provides conventional A.C. power of 110–120 volts to converter 22. This voltage is reduced to 24 volts A.C. and then converted to direct current 24 volts D.C. and converter 22 and has its output coupled to voltage regulator 23 which provides a 13.5 volts direct current output which is connected to a current limiter 24. Current limiter 24 is used to protect power supply 10 and forms an integral part thereof. The overvoltage protection circuit 25 is coupled to the output of current limiter 24. Two controls, the maximum intensity monitor 26 and a maximum timing monitor 27 are provided to control circuit 25, and the output of overvoltage protecting circuit 25 is provided at 28 to produce the regulated 13.5 volts direct current which is provided for all circuits.

Power Supply 10 includes converter 22, regulator 23, limiter 24, overvoltage protection circuit 25 and output 28. The relationship and control of power supply 10 is schematically shown with intensity monitor 26 and timing monitor 27 connected with protection circuit 25.

Figure 3:
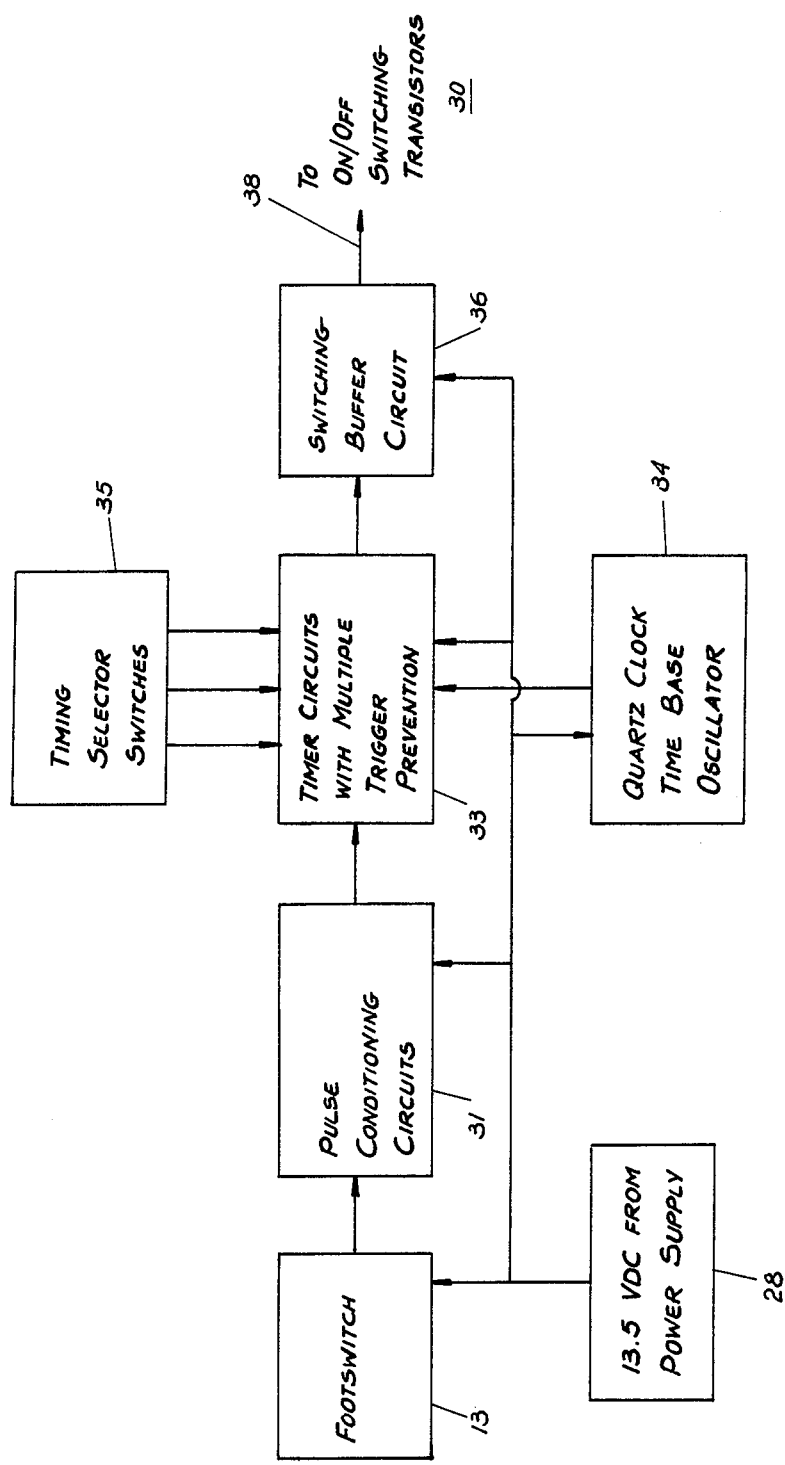
FIG. 3 is a block diagram of the timing circuits to control the length of time the epilator sends RF energy to a hair follicle.

Referring now to FIG. 3 which illustrates the timing circuit 30 coupled to output 28 (FIG. 2) which supplies the 13.5 VDC which is used by all components of circuit 30 and foot pedal switch or footswitch 13 which is connected to timing circuit 30. Timing circuit 30 includes pulse conditioning circuits 31, timer circuits with multiple trigger prevention 33, Quartz clock time base oscillator 34, timing selector switches 35. Footswitch 13 is directly connected with pulse conditioning circuits 31 to provide an output 38 to on/off switches 12, 15 which include switching transistors. Timing circuit 30 also includes timer circuits with multiple trigger prevention 33 which has its time base provided by Quartz clock time base oscillator 34 whose output is connected with trigger prevention 33 which is also coupled with the output of timer selector switches 35. Output of trigger prevention 33 is coupled and input to switching buffer circuit 36.

The timing circuits are used to control the length of time the epilator is sending RF energy to the probe.

Figure 5:
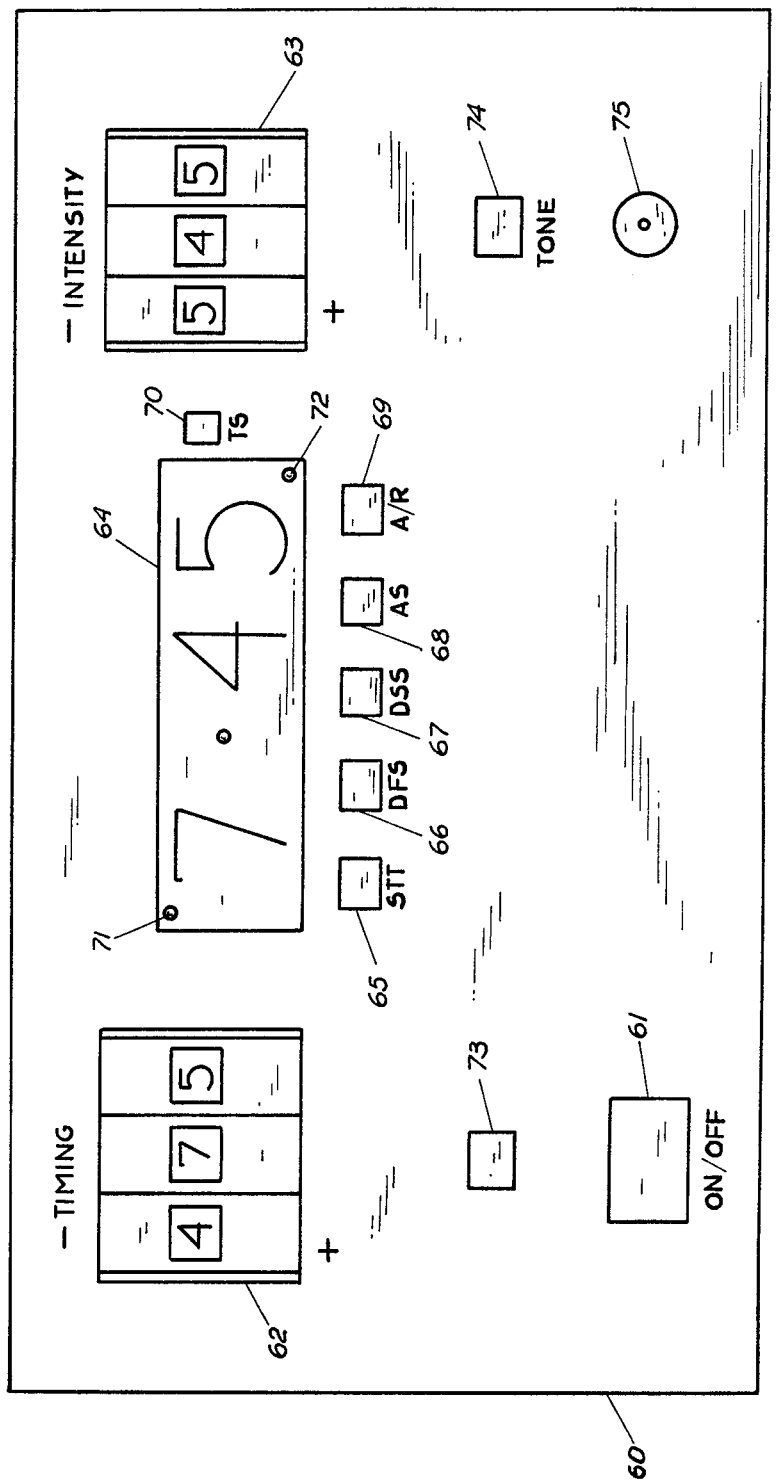
FIG. 5 is a view of the front panel of the epilator apparatus and indicates the controls to be handled by an operator.

The timing circuit 30 uses oscillator 34 which is a 5.12 MH$_z$ quartz clock oscillator as the precision time base generator. This time base signal is then divided 512 to obtain a timing pulse of 1/10,000 of a second (0.0001 sec.) in duration. The timing circuit then counts these pulses until the count adds up to the value, preset by the operator, on the front panel timing select switches 62, see FIG. 5.

In actual operation, the operator pushes the foot pedal switch and the epilator turns on and the counter starts counting pulses. When the count reaches the operator's desired amount, the epilator turns off. The count varies less than 1/10,000 of a second from the preset amount.

The epilation unit can be preset from 0.0 seconds to 0.0999 seconds in increments of 0.0001 seconds. The maximum time available is slightly less than 1/10 of a second.

The timing circuits have other features of note.

First, the footswitch uses an enclosed magnetic reed switch activated by a magnet rather than a mechanically activated unenclosed blade type switch. The unenclosed blade type switch can become unreliable due to dirt and, in some cases, the blade switch must conduct large amounts of current and this may lead to contact failure. The sealed reed switch of this design is protected from environmental hazards and conduct an extremely small aount of current so contact life is very long.

Some designs which use microswitches give an audible click when the operator presses on the foot pedal; some subjects learn to associate the sound with the epilation action and do not relax as they wait for the telltale click. This invention footswitch is silent in operation, maximizing patient comfort. When individuals hear the click, they usually tense up, and this is now avoided.

Second, the pulse conditioning circuits use digital logic designs to prevent variations in the operation of the foot pedal from affecting the timing duration of the epilation pulse. Some operators use a fast, light touch on the footswitch; others use a long, slow touch. With the machine according to the invention, an operator presses the foot pedal for a 0.1 second, but the timer has been set for 0.04 seconds for the pulse, the timer will only output for 0.04 seconds and not 0.1 second.

The pulse conditioning circuits are designed to ignore variations in how the operator acts upon the footswitch. If the operator uses a fast touch, the epilator will still give the selected output. If the operator uses a long, slow touch or even holds the footswitch down continuously, the epilator still delivers only the selected output for only one output pulse. The operator must release the footswitch in order to activate the next pulse.

Some epilator timing circuits, particularly those with long cycles, can give shortened outputs if the operator does not hold the footswitch down for the whole timing cycle. For example, if the operator sets 0.25 seconds as the timing and only depresses the footswitch for 0.1 second, the older design epilator will output a pulse of only 0.1 second. If the operator varies the hold down time, the pulse length can vary from almost no pulse up to 0.25 second. Obviously, this variation will cause variation in treatment effectiveness.

The invention is designed to go to completion, i.e., give the full selected timing cycle, no matter how short the initiation pulse from the operator.

Additionally, some operators "ride" the footswitch and this may cause a string of short uncontrolled pulses to be put out by some of the older design epilators. In the case of the invention, the operator must go to a complete release in order to initiate another timing cycle.

The timer circuit has a built-in protection from being retriggered while in the timing cycle. This means that while the timer is counting during an epilation pulse, the operator cannot extend its timing period by a quick tap on the footswitch, thereby sending the timing circuit another trigger pulse. The timing circuit ignores new trigger pulses until it has completed its timing cycle.

This feature also prevents the timer from giving a continuous group of output pulses in the remote possibility of a failure of the pulse conditioning associated with the footswitch.

The switching buffer circuits protect and isolate the low power timing circuits from the high power switching transistors. This invention gives a high degree of reliability to the epilation unit.

Figure 4:
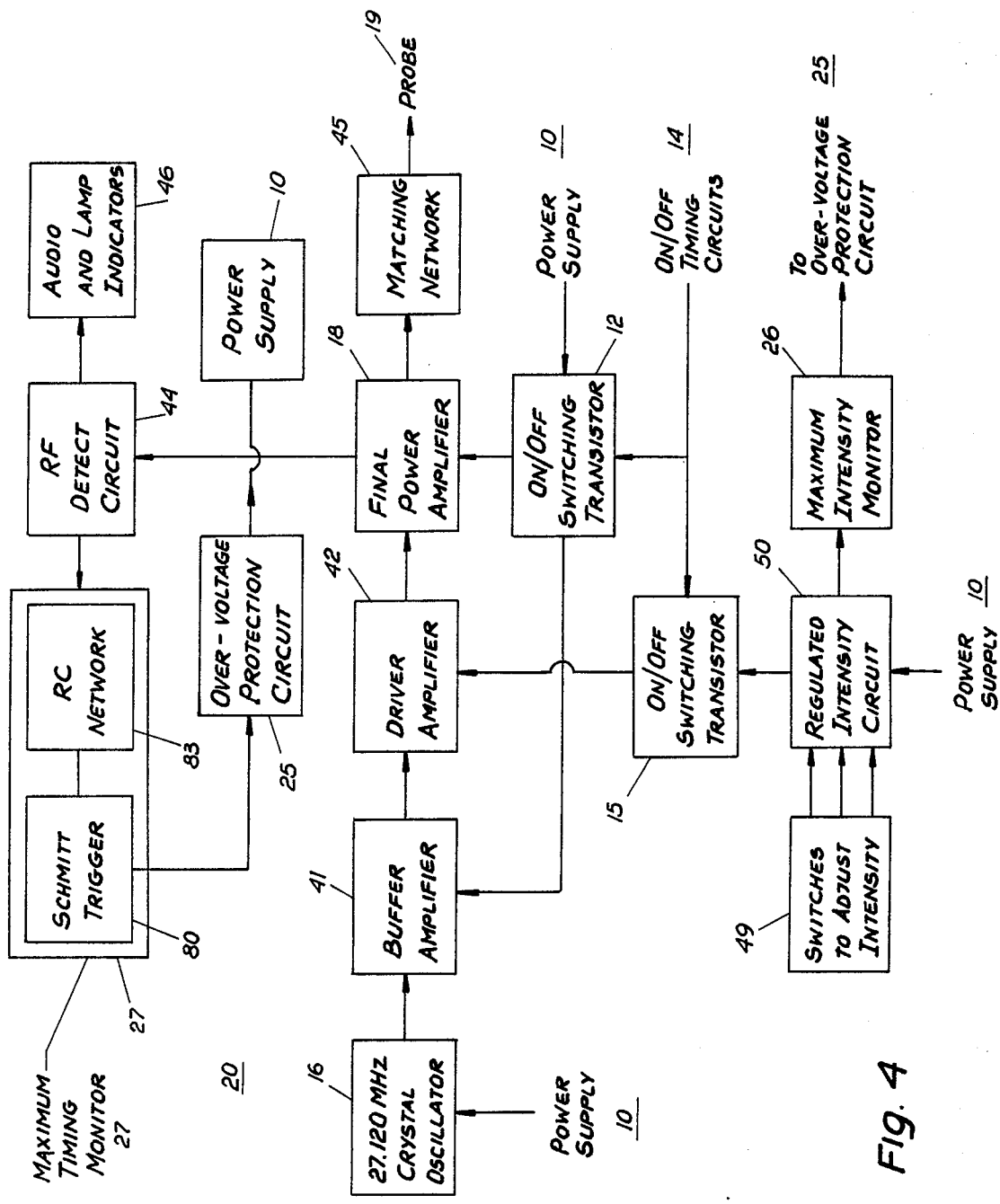
FIG. 4 is a block diagram of the RF section which forms part of the epilator developing the RF energy.

Referring now to FIG. 4 which illustrates the RF-section 20 in detail, and includes oscillator 16 coupled to power supply 10. The output of oscillator 16 which is a crystal oscillator tuned to a 27.120 MHZ frequency and has its output coupled to circuit 17 composed of buffer amplifier 41 and driver amplifier 42. The output of buffer amplifier 41 is coupled to driving amplifier 42, the output of which is coupled to final power amplifier or RF power amplifier 18. Final power amplifier 18 has two outputs, one of which is coupled to RF detect circuit 44 and the other of which is coupled to matching network 45 which in turn is coupled to probe 19. Audio and lamp indicators 46 are coupled to RF detect circuit 44 to show that they are on and a maximum timing monitor 27 has its input coupled to RF detect circuit 44 and its output coupled to overvoltage protection circuit 25, see FIG. 2.

Also coupled to the output of RF detect circuit 44 is the input of an RC Network 83 which has its output coupled to another input to the Schmitt-trigger 80.

The output of Schmitt-trigger 80, as noted in connection with the description of FIG. 1, goes to power supply 10 through overvoltage protection circuit 25, and the power supply 10 is connected with regulated intensity circuit 50 for cutting off power thereto in response to the power supply 10 being shut down. The maximum intensity monitor 26 which includes Schmitt-trigger 80 and voltage divider 81 is coupled to the intensity control 11 (see FIG. 1). Voltage divider 81 has its input coupled to the output of intensity control 11, and its output coupled to Schmitt-trigger 80. The Schmitt trigger 80 is responsive to the output of voltage divider 81 through maximum intensity monitor 26 and is responsive to the output of the RF detect circuit 44 through maximum timing monitor 27, see FIG. 4. While only one Schmitt-trigger 80 is shown, it is possible to use two different Schmitt-triggers, one for the maximum intensity monitor 26 and another for the maximum timing monitor 27.

Intensity control 11 includes switches 49 to adjust the intensity which are used to control regulated intensity circuit 50. The power input to circuit 50 is provided by power supply 10, and the output of regulated intensity circuit is coupled to on/off switching transistor 15 (FIG. 2) which is coupled to buffer amplifier 41 for control thereof. On/off switching transistor 15 is controlled by on/off timing circuits 14, see FIG. 2. Regulated intensity circuit 50 is coupled with maximum intensity monitor 26 (FIG. 2) for monitoring circuit 50 and the output of monitor 26 (FIG. 2) is coupled through Schmitt-trigger 80 to overvoltage protection circuit 25.

A second on/off switching transistor 12 is also energized by power supply 10 and has its input coupled to on/off timing circuits 14 and its two outputs coupled with buffer amplifier 41 and final power amplifier 18.

The front panel 60 includes on/off control 61, timing control indicator 62, intensity control indicator 63, and digital clock timer 64. Other controls on the front panel are STT (set treatment time) 65, DFS (display fast set) 66, DSS (display slow set) 67, AS (alarm set) 68, AR (alarm run indicator) 69, and TS (time set) button 70. Digital clock timer 64 includes AM/PM indicator 71 and alarm "on or off" indicator 72. Audio transducer 73 provides the audio for all tone signals, reference numeral 74 designates RF detect lamp indicator which is coupled to RF detect circuit 44 and is also an on/off switch for RF detect tone. Lamp indicator and switch 74 lights up to indicate presence if RF and the switch portion controls the beeptone. Probe connector 75 is provide for attachment of probe 19.

DESCRIPTION OF OPERATION

Plug female end of an AC cord into male receptacle (labeled 120 VAC) on back of machine. Plug male end of AC cord into any 115 VAC grounded outlet (three conductor outlet). Plug foot pedal cable into Female receptacle (labeled foot pedal) on back of machine. Attach probe holder cord to receptacle marked probe on front of machine. Turn machine on by depressing (on/off) button on switch 61 on front of machine. In the "ON" position the indicator 46 will glow red.

To set the real time display press and hold a red TS (time set) button 70 to the right of the clock 64, while pressing either the DFS (display fast set) 66 or DSS (display slow set) 67. Fast set display increments the display digits at 60 digits per second. Slow set display increments the display digits at 2 digits per second.

When the clock is displaying real time that is PM, a small dot 71 appears in the upper left corner of the display.

The alarm can be set to any time from one minute to 24 hours into the future. To set the alarm, first depress the AS (Alarm Set) button 68. The digits that appear in the display indicate the time that the alarm is currently set for. Using the DFS and/or the DSS buttons 66 or 67 respectively, allows for the adjustment of the alarm time to the desired time. (Note the PM indicator if PM alarm time is desired).

To activate the alarm depress the A/R (alarm-run) button 69 so that the alarm run indicator appears as a small dot 72 in the lower right corner of the display. When the alarm time is reached an intermittant tone is heard until the A/R button 69 is depressed so that the dot disappears from the lower right corner of the display.

These small and precise and repeatable divisions allow the operator to adjust the operation of the epilator to their exact requirements.

The Intensity Selector 63 is also a band of three rocker wheel switches, with 63 the first unit being color coded red and the other two being blue. These rocker wheels function identically to the ones used to control the timing except that they are used by the operator to adjust the level of radio frequency energy that is emitted by the probe.

The range is zero through nine-hundred and ninety nine, thereby giving the operator 999 precise increments to choose from as needed.

The footpedal or footswitch 13 is the control that is used by the operator to start a timing cycle. Once the operator has selected the required timing and intensity settings, then depress the footpedal which activates the epilator's circuitry to deliver the prescribed duration and level of radio frequency energy to the probe 19 and thence to the follicle.

The special electronic features of the footpedal prevent environmental conditions such as dust, dirt and moisture from affecting its consistent operation. In addition circuits prevent variations from occurring in the timing due to different length depressions of the footpedal and double depressions of the footpedal.

A blinking light and beep tone enable the operator to monitor the output visually and audibly. The beep tone may be turned off by the operator.

The elapsed time counter has been included for the timing of treatments of 59 minutes or less. Pressing the STT (Set treatment time) button 65, so that 59 appears in the display. If a 59 minute treatment is to commence, depressing the STT button a second time will begin the elapsed count down. At the end of the 59 minutes a tone will sound continuously for five to eight seconds. If less than 59 minutes are to be counted, the DFS 66 and DSS 67 buttons can be used to set the elapsed timer.

A temporary main AC power failure could cause the clock to give an incorrect display, and the digits in the display will flash on and off.

The timing selector consists of a group of three switches 35, 62 called "rocker wheels". The purpose of the group of switches is to allow the operator to select the duration of time that the radio frequency energy is emitted from the probe and thence into the follicle.

The first of these three switches (from left to right) is color coded red to indicate the most significant change (increase or decrease), with the other two being blue in color. Each rocker wheel is a bidirectional digital control numbered zero through nine. Depressing the top edge of the rocker wheel switch increases the setting. Depressing the bottom edge increases the setting. The range the operator has to choose from is zero through nine-hundred ninety nine, in one ten thousandths of a second divisions. A setting of 999 is equal to one tenth of a second less one ten thousandths (0.0999 seconds or 999/10000). A setting of 475 is equal to 0.0475 seconds or 475/10000.

As best seen in FIG. 4, the oscillator is the only circuit that has D.C. It is not possible to operate without the D.C. The D.C. voltage is 13½ volts with a nominal value of 12 volts. The A.C. is dropped to 24 volts and regulated. The D.C. is adjustable between 11½ to 15 volts ts, but preferred is 13½ volts. With no D.C. the amplifier is shut down. As noted heretofore, the prior art epilators have the amplifier operative when the D.C. is shut down.

The footswitch can also cause oscillation because of the contacts because the blades can fatigue. The gap between the contacts decrease which makes it easier to make a switch closure and causes RF energy to be emitted from the needle. The footswitch used with the apparatus includes a magnetic reed in the switch so that the metal does not fatigue.

The RF detect circuit is a safety circuit to assure that the machine shuts off.

Clock is desirable because the individual being treated sees the time and is assured that they are treated in accordance with the agreed time.

Appropriate filters are also provided to filter out higher harmonics.

These harmonics are filtered out so that there is no interference with other transmitted high frequency signals such as radio and TV.

While there has been shown what is considered to be the presently preferred mode of carrying out the invention, it will be obvious to those skilled in the art that various changes and modifications may be made without departing from the scope of the invention.

We claim:

1. Epilator apparatus for outputting epilator pulses to a germinative portion of hair, comprising:
   an insulated bulbous probe for delivering radio frequency energy to the germinative portion of the hair;
   radio frequency generating means for generating the radio frequency energy and applying the radio frequency energy output from said radio frequency generating means to said probe;
   maximum intensity monitor circuit means coupled to said radio frequency generating means to determine the maximum amplitude of the radio frequency energy output;
   timing monitor circuit means coupled to said radio frequency generating means to predetermine the maximum duration of the radio frequency energy output; and
   power supply means for supplying power to said radio frequency generating means including overvoltage means responsive to said maximum timing monitor circuit means and said maximum intensity monitor circuit means for cutting off power to said radio frequency generating means when a voltage is reached by said intensity monitor circuit means or said timing monitor circuit means in excess of a pre-set value.

2. Epilator apparatus according to claim 1, including controlled footswitch means coupled to said power supply means solely for the activation thereof and to start said timing monitor circuit means, said timing monitor circuit means preventing operator variations and providing a predetermined repeatable control of the time duration of the radio frequency energy output.

3. Apparatus according to claim 2, wherein said footswitch means includes a magnetically operated encapsulated reed switch.

4. Epilator apparatus according to claim 2, including:
   a power amplifier coupled to said radio frequency generating means and to said probe for providing a 27.120 MHz output thereto;
   said power supply means including means to control the power supplied to said power amplifier so that DC current is applied thereto only during application of an epilator pulse by said probe and oscillation is prevented.

5. Epilator apparatus according to claim 4, including timing circuit means for controlling the time duration of the radio frequency pulse such that the duration goes to 0.0999 seconds in increments of 1/10,000 of a second and in less than 0.10 seconds.

6. Epilator apparatus according to claim 5, wherein said radio frequency generating means includes a matching network having an impedance of approximately 850 ohms, and said matching network includes means for connection thereof to said probe.

7. Apparatus according to claim 2, including:
   timing circuits being coupled to said intensity monitor circuit means, said timing monitor circuit means and said footswitch means; and including
   a pulse conditioning circuit to provide a full selected timing cycle to control the duration of the radio frequency output regardless of the duration of the initiation pulse from the operator in response to the operation of said footswitch means, said timing circuits controlling said radio frequency generating means.

8. Epilator apparatus according to claim 1, wherein said radio frequency generating means includes a matching network having an impedance characteristic of the impedance of the germinative portion of the hair.

9. Apparatus according to claim 1, including timing circuits coupled to said intensity monitor circuit means and said timing monitor circuit means and including a pulse conditioning circuit to provide a full selected timing cycle to control the duration of the radio frequency output regardless of the duration of the initiation pulse from the operator, said timing circuits controlling said radio frequency generating means.

10. Apparatus according to claim 9, wherein said timing circuits include means connected to said pulse conditioning circuit and said power supply means to prevent retriggering of a pulse epilation timing circuit by an operator until completion of a previously commenced epilation pulse.

11. Apparatus according to claim 1, comprising display means including:
   an elapsed time indicator coupled to said power supply means for indicating elapsed time from 1 minute to 59 minutes;
   means coupled with said elapsed time indicator for setting the time between 1 minute and 59 minutes; and
   an audible sound indicator connected with said elapsed time indicator for sounding an alarm in response to the elapsed time indicator reaching a pre-set elapsed time.

12. Apparatus according to claim 11, wherein:

said elapsed time indicator includes an alarm clock indicator and is coupled to the output of a clock which includes means to produce an audible tone for a period of five seconds in length continuously when a prescribed amount of elapsed time has expired;

apparatus comprising an audible tone indicator including means responsive to an output from said alarm clock indicator for producing an intermittent tone continuously for a duration of 59 seconds; and said audible sound indicator includes means operatively responsive to said radio frequency generating means to produce a single audible sound per epilation cycle to indicate that said radio frequency generating means is operative to prevent an operator from going through the motions of an epilation procedure with an inoperable machine, thereby tweezing hair.

13. Epilator apparatus as claimed in claim 1, including a probe holder connecting said insulated bulbous probe to said radio frequency generating means to permit ease of removal of said bulbous probe and making electrical connections thereto.

14. Epilator apparatus according to claim 1, wherein:

said radio frequency generating means generates output pulses, the maximum length of the pulse time of each pulse is 0.0999 seconds; and said maximum timing monitor seconds means is pre-set to activate when the radio frequency energy pulse output is for a period longer than 0.140 seconds.

15. In combination, an epilator of the type which includes a radio frequency generating means for generating radio frequency energy, timing circuit means electrically linked to said generator means for controlling the duration of generation of the radio frequency energy, a power supply electrically coupled to said radio frequency generating means, a power amplifier, and an insulated bulbous probe connected to said radio frequency generating means through said power amplifier to produce a degree of heat sufficient to dessicate the germinative area of the hair in response to nearly instantaneous heating action of the radio frequency energy, and including means to prevent self oscillation, comprising:

a preset maximum timing monitor circuit coupled to the output of said radio frequency generating means through a radio frequency detect circuit for predetermining the maximum duration of the radio frequency energy which is output from said radio frequency generating means;

said power amplifier including a stabilizing feedback circuit coupled to said radio frequency generating means for preventing self-oscillation and insuring repeatable operation; and means coupled to said power amplifier to supply d.c. to said amplifier only during the time said probe is operative to supply radio frequency energy to the germinative area of the hair.

16. The combination according to claim 15, wherein the maximum timing monitor circuit includes:

an RC network coupled to the output of said radio frequency detect circuit;

an over-voltage protection network coupled to said power supply; and a Schmitt-trigger coupled to said over-voltage protection network and said RC network to activate said over-voltage protection network to shut down said power supply and thereby said radio frequency generating means to thereby prevent the epilator from out-putting for more than a maximum pre-set time.

17. The combination of claim 15, including:

an over-voltage protection network coupled to said power supply;

an intensity control circuit coupled to and responsive to the output of said power supply;

a maximum intensity monitor including a Schmitt-trigger and a voltage divider, said voltage divider being coupled to the output of said intensity control circuit and to an input of said Schmitt-trigger, the output of said Schmitt-trigger being coupled to said over-voltage protection network, said Schmitt-trigger having a switching point, and said voltage divider maintaining said Schmitt-trigger below its switching point until activated in response to said intensity control circuit causing said voltage divider to permit said Schmitt-trigger to go above its switching point to activate said over-voltage protection network to shut off said power supply; and said maximum timing monitor circuit including an RC circuit and said Schmitt-trigger, said RC circuit being coupled to the output of said radio frequency detect circuit and to said Schmitt-trigger, said RC circuit having an output cycle which when activated for a predetermined period of time causes said Schmitt-trigger to go above its switching point for activating said over-voltage protection network to shut off said power supply.

18. The combination according to claim 17, wherein said switching point is approximately 50% of the supply voltage during normal operation.

19. The combination according to claim 18, including a timing circuit coupled to said pre-set maximum timing monitor circuit, said timing circuit including means having small increments to provide for predetermined and exact levels of treatment that is repeatable for the same time period for different treatments.

20. The combination of claim 15, including:

an over-voltage protection circuit coupled to said power supply and a plurality of easily settable switches having 1000 increments of repeatable intensity.

a regulated intensity circuit coupled to said plurality of easily settable switches to provide said 1000 increments of repeatable intensity; and a maximum intensity monitor circuit having its input coupled to said regulated intensity circuit and its output coupled to said overvoltage protection circuit for rendering said radio frequency generating means inoperative by rendering said power supply inoperative and thereby prevent the epilator from out-putting a voltage in excess of a pre-set value.

* * * * *